United States Patent [19]

Rainford et al.

[11] 4,447,152

[45] May 8, 1984

[54] METHOD AND APPARATUS FOR DETECTING DEFECTS IN APERTURED PLATES

[75] Inventors: Robert E. Rainford, Essex Junction; Mark M. Moser, South Burlington; Jon R. Ojala, Colchester, all of Vt.

[73] Assignee: IBM Corp., Armonk, N.Y.

[21] Appl. No.: 334,183

[22] Filed: Dec. 24, 1981

[51] Int. Cl.³ .............................................. G01N 21/88
[52] U.S. Cl. ..................................... 356/237; 356/378
[58] Field of Search ............... 356/237, 239, 378, 337; 250/562, 563, 572; 350/522, 523, 528

[56] References Cited

U.S. PATENT DOCUMENTS 4,099,881  7/1978  Vanden Broek et al. .......... 356/244
4,319,840  3/1982  Kondo et al. ........................ 356/239

FOREIGN PATENT DOCUMENTS 56-14933  2/1981  Japan ................................... 250/563

OTHER PUBLICATIONS

Kutch, "Inspection Apparatus for Apertured Green Sheets," IBM Tech. Disc. Bulletin, vol. 20, No. 7, Dec. 1977, pp. 2678–2679.

*Primary Examiner*—Vincent P. McGraw
*Attorney, Agent, or Firm*—Pollock, Vande Sande & Priddy

[57] ABSTRACT

A method and apparatus for detecting defects in apertures plates such as masks. The plate is illuminated by a collimated light beam and defects or irregularities are signalled by a bright spot of light. A modified microfilm reader or the like can be used to magnify and project an image of that portion of the plate associated with the bright spot of light.

10 Claims, 3 Drawing Figures

METHOD AND APPARATUS FOR DETECTING DEFECTS IN APERTURED PLATES

DESCRIPTION

1. Technical Field

The invention is concerned with inspection of apertured plates, such as masks. The invention is more particularly directed at rapidly and inexpensively located defects in such apertured plates.

2. Background Art

Manufacture of integrated circuits and other miniaturized electronic components has required the development of precise techniques for pattern transfer using optical techniques or other similar energy masking techniques. A pattern is reproduced in a mask, with dimensions equal to the desired product. The pattern is made up of a series of apertures or holes in a plate with the hole size, or diameter (if circular), critical. The pattern defined in the mask is then used to define areas on an intermediate product for various fabrication steps such as etching, depositing, coating, etc. This pattern transferring process heavily depends upon the accuracy with which the pattern desired to be transferred is reflected in the mask. Accordingly, an essential part of the fabrication process is the inspection of a mask, subsequent to its manufacture and prior to its use or reuse, to ensure that the pattern reflected in the mask is the desired pattern. Unfortunately, these masks may have many features, the size of which are critical to success of the manufacturing process. Inspection is desirable to detect undersized, oversized or contaminated apertures. Manually inspecting a mask having thousands of features is tedious, time consuming and subject to human error. For example, the mask pattern may be optically enlarged, and each feature thereof may be manually compared to a template representing the desired feature size. Repeating this comparison thousands of times for a single mask is a very demanding task.

Attempts have been made in the past to automate the inspection process, one such technique, employing optical filtering is described in Flamholz U.S. Pat. No. 3,746,455; see also Dr. Flamholz's report in the "IBM Journal of Research and Development", November 1973. Both the technique described in the referenced patent and the journal require relatively expensive special equipment including spatial filters, monochromatic light sources and a CRT monitor. Another mechanized inspection technique is illustrated in Southgate, U.S. Pat. No. 4,292,672.

In response to the natural desire to decrease the cost of the inspection function, we have found that effective inspection of apertured plates can be achieved without requiring a coherent light source, spatial filter or CRT. In addition the inspection techniques developed by us can also be effected in a shorter period of time than that required by prior art techniques.

It is therefore one object of the present invention to improve the speed and cost characteristics of inspecting apertured plates such as masks. It is another object of the present invention to perform effective inspection of apertured plates with thousands of apertures in a rapid fashion with a minimal amount of expensive equipment.

In many cases we have found that inspection of an apertured plate such as a mask will reveal one or more features or holes which are blocked or partially blocked due to debris which can be easily dislodged, if the debris can be located. Accordingly, our inspection method and apparatus can be extended to include apparatus and/or steps to dislodge the dibris, once it is located. Therefore, it is another object of the present invention to provide an inspection/cleaning apparatus which is capable of rapidly and inexpensively locating defects in an apertured plate, and, once irregularities have been located, to direct a cleaning apparatus at that location to dislodge any debris which may be the cause of such irregularities.

SUMMARY OF THE INVEVTION

We have found that an apertured plate such as a mask can be readily visually inspected to rapidly locate irregularities with the use of relatively inexpensive equipment. The mask may be supported in a position so that it can be illuminated by an intense polychromatic light source; dispensing with the requirement for a monochromatic light source is a significant factor in reducing the expense of the inspection operation. The mask is oriented so that the light is directed perpendicular to the major dimension of the mask and parallel to the axis of the plurality of apertures therethrough. Defects or irregularities in the mask can then be readily visually detected by viewing the light transmitted by the mask at an angle of about 30°–60° to the plane of the major dimension of the mask. In order to bring all of the aperatures into the observer's field of view, the mask may be rotated about an axis parallel to the axis of the apertures, and in the plane of the major dimension of the mask. Defects or irregularities are revealed as one or more bright spots, even though the absence of magnification means that the viewer cannot actually see the cause of the defect or irregularity.

Once having located a defect or irregularity, the mask may be placed in a conventional microfilm reader or other optical projector; the area in which the defect or irregularity is located is magnified. The magnified image can then be visually compared with the template to verify the presence of a defect or irregularity.

Optionally, if the inspection method and apparatus is associated with a cleaning step or apparatus, once a defect or irregularity has been located, a jet of cleaning fluid may be directed at that location to dislodge any debris which may be the cause of the defect or irregularity.

Therefore, in accordance with one aspect the invention provides:

A method of inspecting apertured plates comprising:
directing an intense polychromatic light beam perpendicular to a major dimension of the plate and parallel to axes of apertures in the plate,
viewing the beam passing through the apertures at an angle of between 30° and 60° to the plane of the major dimension of the plate,
whereby defects or irregularities are located by observing irregularities in the pattern of light transmission.

In accordance with another aspect the invention provides an inspection apparatus for inspecting apertured plates comprising:
an intense polychromatic light source,
means for collimating light emitted from said source for forming a collimated light beam having a designated path, and
support means for supporting an apertured mask in the path of said beam.

In accordance with further features of the latter aspect of the invention, means may be provided for rotating the support so that each of the apertures in the plate can be brought within a desired field of view. In addition, a projector can be associated with the inspection apparatus for projecting an enlarged image of a region of the mask in which defects or irregularities are located. As a further optional feature a source of cleaning fluid may be associated with the projector so that the source can be directed at areas of the mask in which defects or irregularities are located.

In a like fashion, the first mentioned aspect of the invention may be further associated with an addition step of rotating the plate through 360° to observe each of the apertures with respect to said beam at said angle.

BRIEF DESCRIPTION OF THE DRAWINGS

The invention will now be described in such detail as to enable those skilled in the art to make and use the same in the following portions of this specification when taken in conjunction with the attached drawings in which.

DESCRIPTION OF PREFERRED EMBODIMENTS

Figure 1:
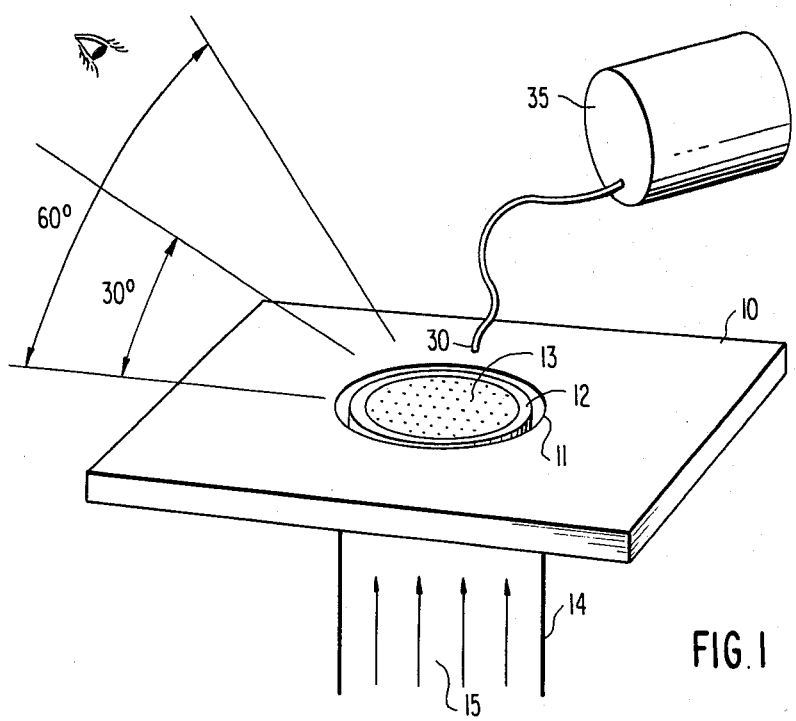
FIG. 1 is a schematic illustrating the inventive apparatus.

FIG. 1 is a part perspective, part schematic illustration useful in explaiaining the method aspects of the invention and describing the apparatus. As shown in FIG. 1, 10 refers to a support, which has an aperture 11 therein within which a mask 12 can be supported. The mask 12 includes apertures therein, aperture 13 representing a single aperture. These apertures may be circular holes, rectangular apertures, or the like. For example, a mask may have 600 holes of 0.1 mm diameter. The mask 12 has a major dimension which is generally parallel to a major dimension of the support 10, i.e. for example both may have major dimensions in a horizontal plane, when the mask is oriented as shown in FIG. 1. While the apertures 13 may be of varying cross section, they all have axes which are normal to the plane of the mask 12. For ease of description, we refer to the plane of the mask as that plane within which a major dimension of the mask lies. The aperture 11 and mask 12 are located so that a collimated polychromatic light beam 15 is directed perpendicular to the plane of the mask and parallel to the axes of each of the apertures. The light beam can, for example, be confined in a column defined by a cylindrical wall 14.

With the mask located on the support 10 so as to be illuminated by the light beam 15, defects or irregularities can readily be identified in the mask 12 by an observer, schematically depicted in FIG. 1, viewing the mask 12 at an angle between 30° and 60° to the plane of the mask. Under these circumstances, defects or irregularities will show up as a bright spot.

In order to view the entire surface of the mask 12, and all the apertures 13, at the appropriate angle the mask 12 may be rotated on the support 10 during the observation. The observation angle is preferably in the range of 30° to 45° to the plane of the mask 12. However, we have found that such rotation is not required especially if the mask can be translated in one or preferably two dimensions during the viewing step.

Auxiliary apparatus may be used to further enhance the inspection operation. Such auxiliary apparatus can include a modified microfilm reader. The microfilm reader has associated with it a viewing lens that can be positioned variably with respect to a viewing stage. Preferably, the viewing stage of the microfilm reader is the support 10. The support 10 is moveable between two positions; in a first position the mask can be examined for the presence of a bright spot indicative of an irregularity, in the second position a portion of the mask area can be magnified by the modified microfilm reader. In the first position, the operator can position the mask (in two dimensions) so as to locate any bright spots (indicative of defects or irregularities) relative to a fixed pointer assembly. The modified microfilm reader also includes a marker pen and a second pointer, fixed relative to each other and moveable with the support 10. The distance between the marker pen and second pointer is equal to the distance between the first pointer and the viewing lens. Accordingly, when the operator positions the first pointer relative to any bright spot, he also operates the pen to record the relative position. Thereafter, to magnify the now located area of the mask, the viewing stage is moved relative to the viewing lens until the second pointer overlies the mark made by the pen. Because of the pre-established relation between the first pointer and viewing lens, and the pen and second pointer, when the second pointer overlies the mark made by the pen, the viewing lens overlies the area of the mask in which a potential defect or irregularity has been noted. The operator can then readily determine from the magnified image, whether or not the defect or irregularity is within the mask tolerances. For example a template can be used in a go/no go measurement. In addition, since the mask using process may result in debris adhering to a mask, it may be possible to remove the defect or irregularity if it is occasioned by debris which can be dislodged. To this end, a source of a cleaning fluid such as a compresesed air tank 35 is associated with the microfilm reader. With the use of a combination fiber optic pointer and air nozzle 30, the operator can direct a jet of such cleaning fluid (compressed air for example) at the region on the mask in which the defect or irregularity is located. If the defect or irregularity is occasioned by debris which can be dislodged by the cleaning jet, the operator can readily effect this function.

Figure 2B:
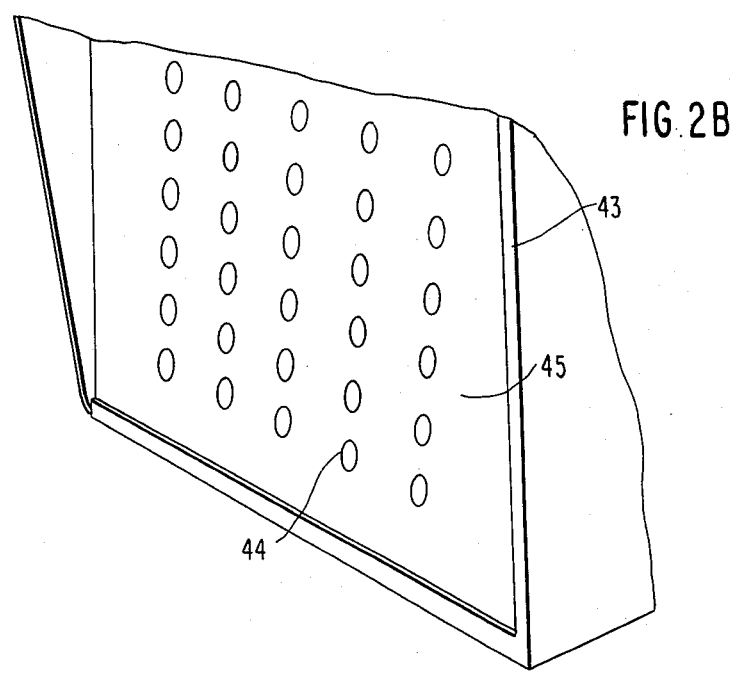
FIG. 2B is a representation of an image formed by a projector for precise determination of mask characteristics vs. a template in accordance with the invention.
Figure 2A:
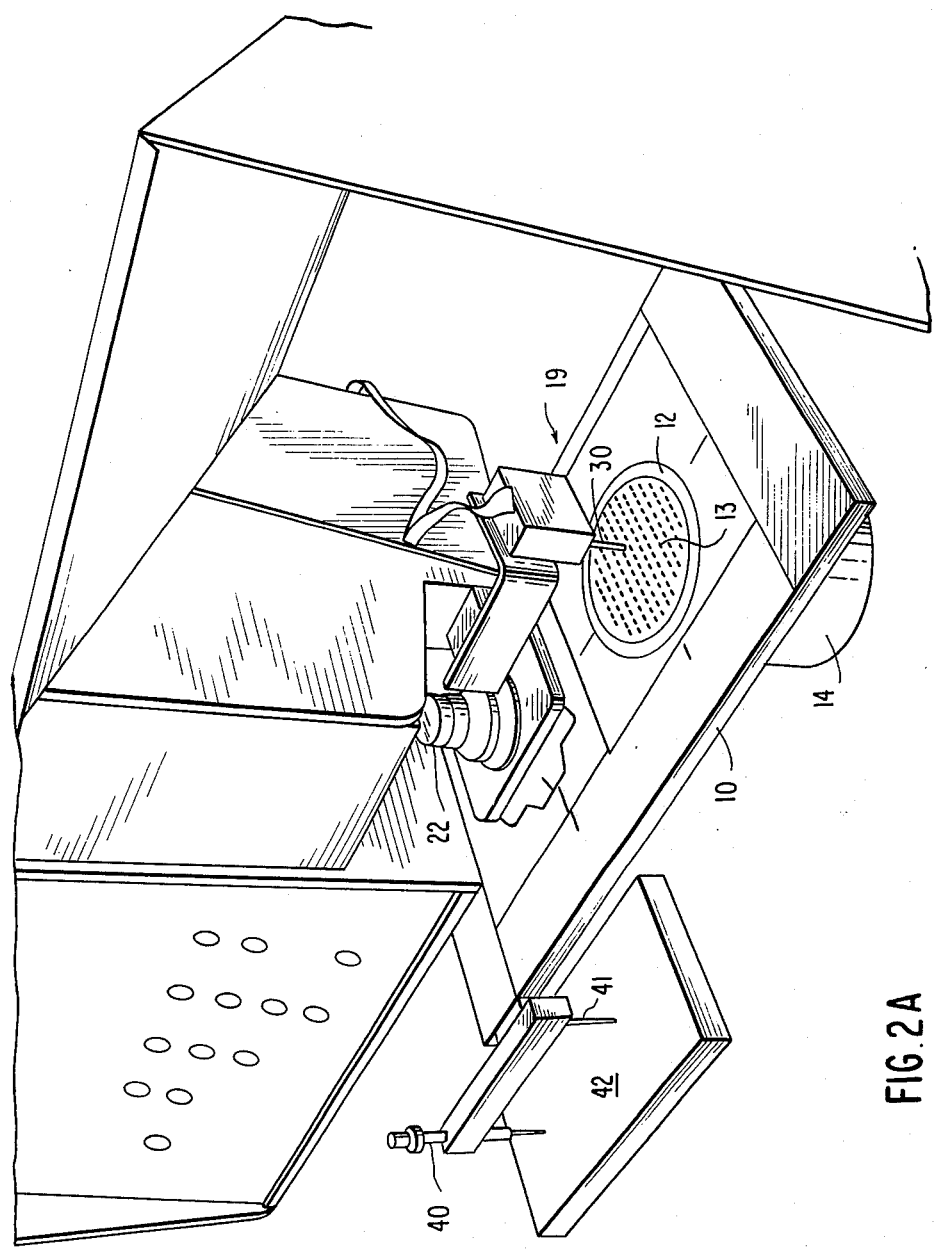
FIG. 2A is a three-dimensional view of one embodiment of the invention.

FIG. 2A is an illustration of an apparatus which has been constructed in accordance with the present invention. FIG. 2A illustrates the columnar light beam conducting cylinder 14 associated with the support 10, on which is located a mask 12 including a plurality of apertures 13. The viewing lens 22 overlies that portion of the stage 10 corresponding to the mask's second position. The pointer assembly 19 includes the first pointer 30, and as is seen in FIG. 2A, is fixed over the mask's first position. The mask's location relative to the pointer 30 is variable in that the mask 12 can be moved (in two dimensions, parallel to the plane of the mask 12).

Also attached to the stage 10 is a pen 40 and a pointer 41. Located directly beneath the pen and second pointer is a record sheet 42, i.e. any object which is fixed and on which the pen 40 can be used to make a visible mark. The distance between pen 40 and second pointer 41 is equal to the distance between the first pointer 30 and the viewing lens 22.

In operation, the operator positions a mask 12 in the stage 10, located in its "first position", that is generally underlying the pointer assembly 19. A polychromatic collimated light beam illuminates the mask 12. The source of this light beam is located within the cylinder 14. Any defects or irregularities, indicative of potential out-of-tolerance condition of any of the mask apertures, or debris adhering the mask, will be observed by the operator as a birght spot of light when the mask is viewed by the operator at the appropriate angle.

When the operator notes one or more such bright spots, the mask 12 is positioned so that the fixed pointer 30 overlies a bright spot. At the same time, the pen 40 is depressed so as to make a mark on the record 42. Subsequently, the mask 12 is moved from its first position to its "second position", by translating the stage 10 under the viewing lens 22. Since the pen and second pointer 41 are fixed relative to the stage 10, this moves the pointer 41 in the general vicinity of the mark made by the pen 40 on the record 42. The stage 10 is then translated in two dimensions so as to bring the second pointer 41 into coincidence with the mark made by the pen 40 on the record 42. This ensures that the viewing lens 22 directly overlies the area on the mask 12 which had been associated with the bright spot when the mask was in its first position. This results in a magnified image of that portion of the mask 12 on the screen of the microfilm reader. The screen of the microfilm reader may have associated with it a template with indicia theron indicating to the operator the desired mask characteristics, for example aperture size and spacing, etc. By comparing the magnified image of the selected portion of the mask 12 with the template, the operator can readily determine if the mask is either within or without tolerance.

Preferably, the first pointer 30 may actually comprise a hollow tube coupled to a source of a cleaning fluid such as the tank 35 shown in FIG. 1. The operator can then, first flush the mask 30 with a jet of cleaning fluid in an attempt to dislodge any debris. This operation can be effected prior to projecting an image of the mask 12, or subsequent thereto.

In a preferrred embodiment of the invention, the polychromatic light source comprised 150 watt, 24 volt Norelco bulb carrying the commercial designation FD5. In that same embodiment, the diameter of the light cylinder 14 was sized relative to the diameter of the mask 12 and the column 14 has a length of 3.5 inches.

FIG. 2B represents the screen 51 of the microfilm reader. As shown in FIG. 2B the reader magnifies an image of a portion of a mask 12 including apertures 13 therein. The image of the apertures 13 is represented in FIG. 2B by the aperture images 44. A template with appropriate indicia can then be overlaid over screen 51 to allow the operator to readily determine the go/no go condition of any aperture. Typically the reader parameters are arranged so that the entire screen 51 represents only a small fraction of the entire mask. The operator can readily pick out the irregularity in the image representing the mask irregularity.

Accordingly, it should now be apparent that the invention provides a method and apparatus for readily detecting irregularities in an object with a plurality of apertures therethrough. The apparatus is relatively inexpensive, especially compared to prior art devices used to achieve the same purpose, and lifts the burden from the operator of optically reviewing the entire mask area. Instead, the absence of any bright spot on the mask 12 when illuminated by a polychromatic collimated light beam indicates the absence of any defects or irregularities and eliminates the necessity for the operator to optically review any portion of the mask 12. In the event that one or more bright spots are seen by the operator, he then need only optically view that portion of the mask associated with each of the bright spots. The use of the modified microfilm reader, and the apparatus used to position the viewing lens relative to the mask allows the operator to readily magnify selected portions of the mask for optical viewing.

It should be apparent to those skilled in the art that many changes can be made to the preferred embodiment illustrated herein within the spirit and scope of the invention. More particularly, we have illustrated an apparatus in which the viewing lens 22 is fixed and the mask is moved relative to the viewing lens to magnify and project selected areas of the mask 12. Conversely, it is also possible to fix the position of the mask and move the viewing lens 22 relative to the mask to magnify and project selected areas of the mask 12. In some embodiments of the invention, we have arranged the support for the mask 12 so that it could be translated in two dimensions parallel to the plane of the mask, and also rotated in the same plane. While we have indicated above that we have now determined that rotation is not necessary, it should also be apparent that rotation can also be allowed.

We claim:
1. The method of inspecting an apertured plate comprising:
   directing an intense polychromatic collimated light beam perpendicular to a major dimension of said plate and parallel to axes of apertures therethrough,
   viewing the beam passing through the apertures at an angle of between 30° and 60° to the plane of a major dimension of the plate,
   whereby defects or irregularities in the plate or said apertures result in one or more bright spots.
2. The method of claim 1 which includes a further step of rotating said apertured plate through approximately 360° to observe each of the apertures with respect to said beam at said angle.
3. The method of claims 1 or 2 which includes the further step of:
   locating at least one said bright spot,
   locating said apertured plate in a magnifying apparatus and magnififying a selected portion of said plate in the vicinity of said bright spot to produce a magnified image of said selected portion.
4. The method of claim 3 which further includes comparing said magnified image with a template.
5. The method of claim 1 or 2 which includes the further step of directing a jet of cleaning fluid at apertures in the vicinity of said bright spot.
6. An inspection apparatus for inspecting apertured plates comprising:
   an intense polychromatic light source,
   collimating means for collimating light emitted from the source and forming a collimated light beam having a designated path, and
   support means for supporting said apertured plate in the path of and substantially perpendicular to said beam so as to allow said mask to be viewed from a relatively fixed observation location with the mark in at least two different positions relative to said observation location.

7. The apparatus of claim 6 which further includes projection means for enlarging and projecting the image of a selected portion of said plate.

8. The apparatus of claim 6 or 7 which further includes a source of a compressed fluid,
and means for projecting a fluid jet through an aperture of said plate when contamination is observed in said aperture.

9. The apparatus of claim 7 which further includes a registering means for locating said apertured plate in a predetermined position relative to said projection means.

10. The apparatus of claim 9 in which said projection means comprises a projection screen and a viewing lens and said registering means comprises a pen and pointer fixed in relation to each other.

* * * * *

UNITED STATES PATENT AND TRADEMARK OFFICE
CERTIFICATE OF CORRECTION

PATENT NO. : 4,447,152
DATED : May 8, 1984
INVENTOR(S) : Robert E. Rainford, Mark M. Moser and Jon R. Ojala It is certified that error appears in the above-identified patent and that said Letters Patent is hereby corrected as shown below:

On the title page

Abstract, lines 1-2, change "apertures" to -apertured-.

Col. 1, line 9, change "located" to -locating-.

Col. 2, line 2, change "dibris" to -debris-.

Col. 3, line 13, change "addition" to -additional-;

line 34, change "explaianing" to -explaining-.

Col. 5, line 8, after "adhering" insert -to-;

line 9, change "birght" to -bright-;

line 65, change "inexpansive" to -inexpensive-.

Signed and Sealed this

Ninth Day of October 1984

[SEAL]

Attest:

GERALD J. MOSSINGHOFF

Attesting Officer
Commissioner of Patents and Trademarks